United States Patent
Stevens et al.

(10) Patent No.: US 6,878,521 B1
(45) Date of Patent: Apr. 12, 2005

(54) FIBRIL-BLOCKING PEPTIDE, A METHOD FOR PREVENTING FIBRIL FORMATION

(75) Inventors: Fred J. Stevens, Naperville, IL (US); Yair Argon, Flossmoor, IL (US); David P. Davis, Chicago, IL (US); Rosemarie Raffen, Elmhurst, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 09/712,819

(22) Filed: Nov. 13, 2000

Related U.S. Application Data (60) Provisional application No. 60/165,424, filed on Nov. 14, 1999.

(51) Int. Cl.$^7$ ................. G01N 33/53; G01N 33/576; A61K 38/08
(52) U.S. Cl. ............. 435/7.1; 435/7.21; 435/326; 530/329
(58) Field of Search ............... 435/7.1, 7.21, 435/69.3, 326, 331; 424/185.1, 9.2, 142.1; 530/329

(56) References Cited

U.S. PATENT DOCUMENTS 5,276,059 A * 1/1994 Caughey et al.

OTHER PUBLICATIONS

Ngo et al., 1994, The Protein Folding Problem and Tertiary Structure Prediction, pp. 492–495.*
Stryer et al, in Biochemistry, Third edition, W H Freeman Company, New York, pp. 31–33, 1998.*
Boland et al, J Biol Chem 271: 18032–18044, 1996.*
Peterson et al, Proc Natl Acad Sci USA 95: 12956–12960, Oct. 1998.*
Davids et al, J Immunology 163: 3842–50, Oct. 1999.*
Gardner et al, J Biol Chem 268(34): 25940–47, 1993.*
Boland et al, J Biol Chem 271(30): 18032–44, 1996.*
Schubert et al, European J Neuroscience 9: 770–777, Apr. 1997.*
Ohashi et al, Virchows Arch 428(1): 37–46, Apr. 1996.*
Stevens et al, Cell Mol Life Sci 57(3): 441–9, Mar. 2000.*
Davis, et al, "Inhibition of Amyloid Fiber Assembly by Both BiP and its Target Peptide," *Immunity* Oct. 2000, pp. 433–442, vol. 13, Cell Press.

* cited by examiner

*Primary Examiner*—Christina Chan
*Assistant Examiner*—Phuong Huynh
(74) *Attorney, Agent, or Firm*—Cherskov & Flaynik (57) ABSTRACT

A method of minimizing the aggregation tendencies of an amyloid forming protein is provided comprising identifying a portion of the protein that is critical to amyloid formation; and inserting a peptide at the portion. The invention also provides a peptide for insertion in an intact human kappa-IV light chain variable domain, the peptide comprising the following amino acid sequence $Phe_{71}$-$Thr_{72}$-$Leu_{73}$-$Thr_{74}$-$Ile_{75}$-$Ser_{76}$-$Ser_{77}$ (SEQ ID NO. 1) wherein the subscript numbers are the residue location points in the domain. A method for preventing amyloid formation in human kappa-IV light chain variable domain is also provided, the method comprising inserting the peptide $Phe_1$-$Thr_{72}$-$Leu_{73}$-$Thr_{74}$-$Ile_{75}$-$Ser_{76}$-$Ser_{77}$ (SEQ ID NO. 1) into the domain, wherein the subscript numbers indicate the residue location on the domain.

7 Claims, 4 Drawing Sheets

FIBRIL-BLOCKING PEPTIDE, A METHOD FOR PREVENTING FIBRIL FORMATION

This Application is based on Provisional Patent Application 60/165,424 filed on November 14, 1999.

BACKGROUND OF THE INVENTION

1. Field of the Invention

This invention relates to a fibril-preventing peptide and a method for preventing the formation of fibrils and more particularly, this invention relates to a peptide and a method for preventing the formation of solid protein structures and disease associated therewith.

2. Background of the Invention

"Conformational diseases," share a common etiology whereby proteins fold irregularly to produce structural flaws. These flaws result in the proteins unnaturally aggregating and thereafter precipitating as fibrils from their solvents. Such solvents include blood, urine, water, lymph, cerebrospinal fluid, and other physiological fluids. Diseases such as sickle cell anemia, amyloid light chain disease, senile systemic amyloidosis, Alzheimer's, and prion encephalopathies including kuru and "mad cow" disease or BSE, are the result of protein conformation anomalies.

The immunoglobulin light chain (LC) is normally a soluble, secreted protein, but some light chains aggregate into ordered fibrils with characteristics similar to other amyloid deposits. Among the human immunoglobulin variable domain ($V_L$) sequences known to form amyloid fibers, somatically mutated derivatives of a small number of germline genes are over-represented. One of these is kappa-IV, many of whose derivatives are associated with light chain amyloidosis. The tendency of kappa-IV sequences to form fibrils is inversely correlated with their thermodynamic stability, and while both stabilizing and destabilizing mutations are found in amyloidogenic kappa-IV sequences, only destabilizing mutations promote fibril formation.

The inventors have found that the conformational change required to convert a soluble light chain into a fibrillogenic variant can be caused by single somatic mutations. Importantly, an aggregating light chain can nucleate fibril formation of a soluble light chain when sufficient sequence compatibility exists. This has important implications in the context of ongoing hypermutations, whereby multiple light chain sequences are generated.

Fibril deposition and build-up in tissues is the underlying mechanism of a number of diseases for which no drug therapy currently exists. However, research has shown that flufenamic acid inhibits the conformational changes of transthyretin which is associated with amyloid fibril formation. S. A. Peterson et al. *Proc. Natl. Acad. Sc. USA* (Oct. 27, 1998) 95(22): 12956–60.

Once fibril build-up occurs, often the only intervention is surgical whereby the over-ladened tissue has to be modified or else removed.

A need exists in the art for a substance and process to stymie the in vivo precipitation of protein. The substance and process should incorporate physiologically compatible materials and require no invasive procedures common with more typical treatments of protein deposit diseases.

SUMMARY OF THE INVENTION

It is an object of the present invention to provide a treatment modality for conformational disease that overcomes many of the disadvantages of the prior art.

It is another object of the present invention to provide a protocol to stymie the development of fibrils. A feature of the invention is the strategic insertion of a peptide molecule in the subunits of deposition-likely proteins. An advantage of the invention is that the insertion prevents fibril formation in the first place, and therefore minimizes morphological tissue changes otherwise associated with deposition accumulation.

Yet another object of the present invention is to provide a substance to aid in the treatment of conformational diseases. A feature of the substance is that it contains an amino acid sequence contained in variable domain regions of proteins which aggregate and subsequently precipitate. An advantage of the substance is that its presence in the various domain regions blocks the domain swapping of the protein with similar light chains and therefore blocks or inhibits the protein aggregation which causes protein precipitation.

Briefly, the invention provides a method for minimizing the aggregation tendencies of an amyloid forming protein, the method comprising identifying a first amino acid sequence of the protein that is replaced by a second amino acid sequence during physiological conditions (e.g., in vivo); and preventing the replacement by juxtaposing a peptide to the first amino acid sequence.

The invention provides a method for preventing amyloid formation in human kappa-IV light chain variable domain by inserting the peptide $Phe_{71}$-$Thr_{72}$-$Leu_{73}$-$Thr_{74}$-$Ile_{75}$-$Ser_{76}$-$Ser_{77}$ (SEQ. ID. NO. 1) into the domain, wherein the subscript numbers indicate the residue location on the domain.

The invention provides a peptide for insertion in an intact human kappa-IV light chain variable domain, the peptide comprising the following amino acid sequence:

$Phe_{71}$-$Thr_{72}$-$Leu_{73}$-$Thr_{74}$-$Ile_{75}$-$Ser_{76}$-$Ser_{77}$ (SEQ. ID. NO. 1)

Also provided is a method for preventing fibril assembly, the method comprising identifying a region of a first aggregating protein moiety that normally interacts with a second protein moiety to form the assembly; and juxtaposing a binding protein to the first moiety.

BRIEF DESCRIPTION OF THE DRAWING

These and other objects and advantages of the present invention can be better understood from the accompanying drawings whereby.

DETAILED DESCRIPTION OF THE INVENTION

Generally, the invented method involves identifying submotifs in primary structures that are critical in fibril formation, and then inserting a small biological-molecule inhibitor that stabilizes the normal conformation of a protein. The biological molecule (e.g. a peptide antagonist) functions by blocking the site involved in the interchange of domain segments. A myriad of primary structures are suitable, including but not limited to, unnatural amino acids, peptides, which may be modified to change solubility characteristics, the use of D-amino acids versus L-amino acids, and substances not readily metabolized by the body. For the sake of illustration, subunits of human proteins are utilized herein as the amyloid inhibiting agents.

A thorough discussion of stymying amyloid formation via the invented method is found in D. P. Davis, et al., *Immunity* 13, 433–442 (2000), and incorporated herein by reference.

The inventors utilized an ensemble of kappa-IV somatic mutants as an experimental system to dissect how individual mutations promote the formation of amyloid fiber by light chains and then devised ways to inhibit this reaction.

As described in more detail infra, the inventors demonstrate that in vitro fibril formation by light chain variable domains ($V_L$) is blocked by selected peptide insertion and binding protein (BiP) insertion. (BiP is the endoplasmic reticulum chaperone involved in directing normal folding of $V_L$.) It was also found that fibril formation is inhibited by a peptide derived from a portion of the $V_L$ involved in BiP binding.

The inventors discovered that light chains form fibrils through a folding intermediate involved in inter-protein loop swapping. The exposure of the mobile loop, due to a conformational anomaly, may mediate "loop swapping" with other monomers, nucleating fibril formation. Experimental data show that fibril formation is a nucleation-mediated reaction, where the formation of the nuclei is rate-limiting, presumably due to the unfavorable conformational change required in the aggregating unit (such as a $V_L$ dimer).

A linear peptide is provided herein which blocks such swapping (and therefor the aggregating) of antibody light chain variable domains. The peptide corresponds to a fragment of intact protein which typically aggregates with another domain to create a dimer. Specifically, the inventors have identified a peptide having a sequence similar to positions 71 through 77 of the human kappa-4 light chain variable domain. The functional sequence is as follows:

$$\text{Phe}_{71}\text{-Thr}_{72}\text{-Leu}_{73}\text{-Thr}_{74}\text{-Ile}_{75}\text{-Ser}_{76}\text{-Ser}_{77} \text{ (SEQ ID NO. 1)}$$

wherein the subscript numbers are the residue location points in the domain.

The above peptide, when inserted into the core of the aggregating-prone variable domain, provides major anchorage for a hairpin turn spanning residues from position 60 through 83 in the protein. The inventors have found that without an intact anchoring or attachment-point of the hairpin to the core domain, the hairpin detaches itself from the core domain and attaches itself to another domain. Likewise, the cavity remaining in the core domain would be filled by a detached hairpin from another core protein. It is this "domain swap" between core protein domains which results in the formation of highly stable fibrillar assemblies.

Figure 1:
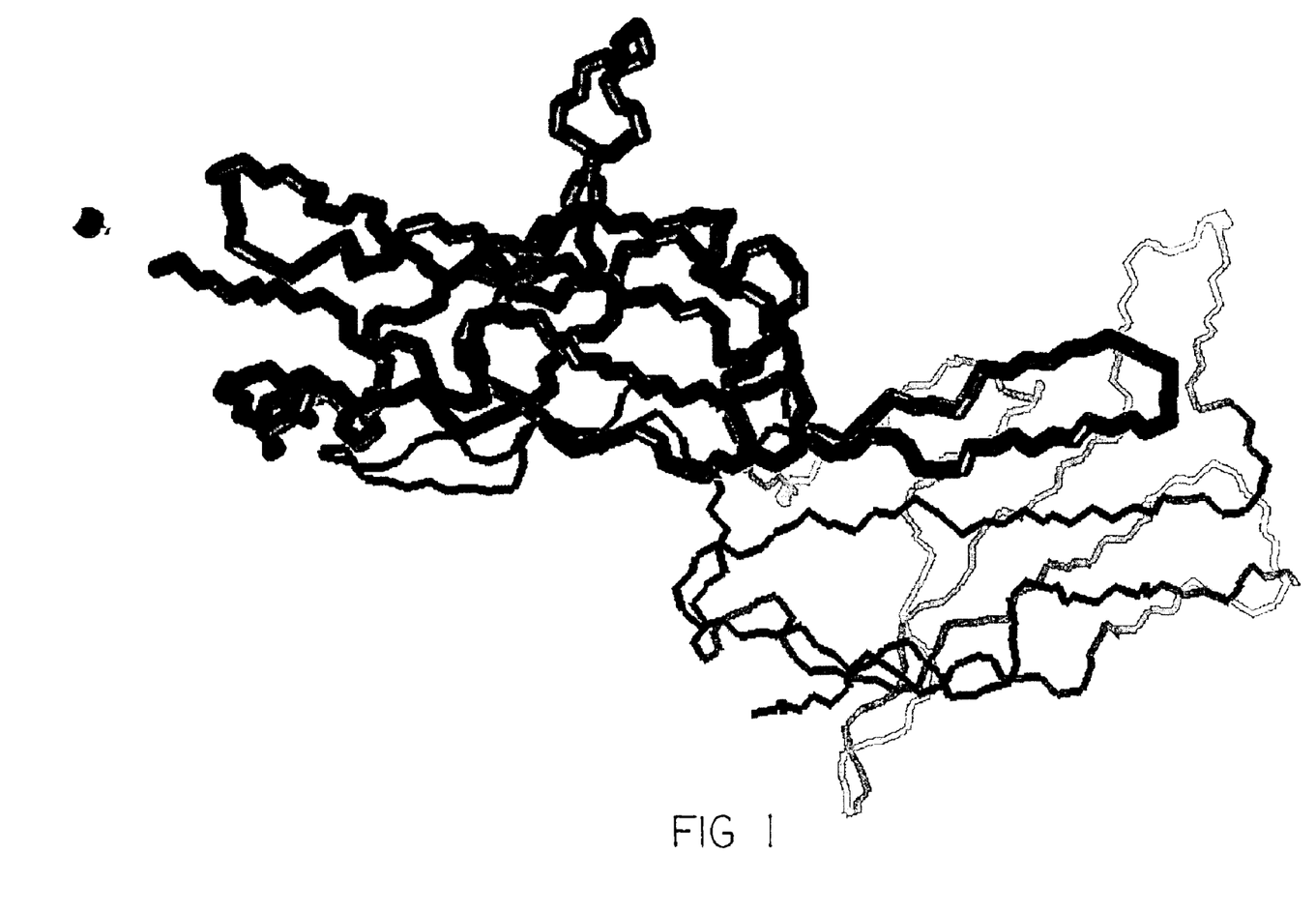
FIG. 1 is a computer-generated diagram of a hypothetical "Domain Swap" involved in an early step of fibril formation by antibody light chain variable domains.

Mutations which compromise a highly conservative ionic interaction between residues at 15, positions 61 and 82 are highly correlated with amyloidosis, possibly by compromising the interaction between the hairpin and the domain core. If this interaction is stymied, the hairpin turn readily diffuses away from the core of the domain. This provides an opportunity for the extruded portion (component A) of the protein to insert itself into the corresponding portion of a second molecule (component B). Likewise, the cavity formed in A could be filled by the extruded portion of component B, resulting in an AB dimer in which the polypeptide chains are intermingled. Such intermingling of domains A and B is schematically illustrated in FIG. 1. Further, because the peptide is identical in composition to a portion of the light chain variable domain that is critical for stable packing of the molecule, the observation suggests that it may be possible to generalize this strategy of structural mimicry to develop other peptides that may serve as antagonists (inhibitors) of other conformational disease processes.

The mechanism outlined above also applies to other amyloidogenic proteins that share with variable domains a structural motif known as a "greek key." This motif is characterized by a so-called beta sheet sandwich in which one or more of the hairpin turn structures are found. Amyloid forming proteins such as antibody constant domains, transthyretin, and beta-2-microglobulin are all members of the aforementioned motif and it may be appropriate to collectively describe this class of amyloid forming proteins as constituting the "greek key amyloidoses." Additionally, serpins (serine protease inhibitors) while not formally greek key proteins, are amyloid forming proteins known to be capable of domain exchange. It is possible that peptides which mimic appropriate portions of the internal structure of any of these proteins may be effective in inhibiting fibril formation. Although the composition of therapeutic peptides are likely to be disease-specific, the approach to developing the therapeutic agents should be common to all "greek key amyloidoses."

For the sake of this disclosure greek key fold proteins include, but are not limited to, and antibody constant domains, transthyretin, beta-2-microglobulin, serine protease inhibitors, and crystalline.

Further, the inventors used an agitation-based in vitro assay to assemble fibrils from two kappa-IV recombinant $V_L$, LEN and SMA. LEN was derived as a Bence Jones protein and is a soluble, stable protein, differing from the germline kappa-IV by only one somatic mutation. (FIG. 1*a* in Inhibition paper). In contrast, SMA formed thioflavin T-binding, Congo red-positive fibrils even without GuHCl.

Heptameric Peptide

Inhibition Detail

Figure 2:
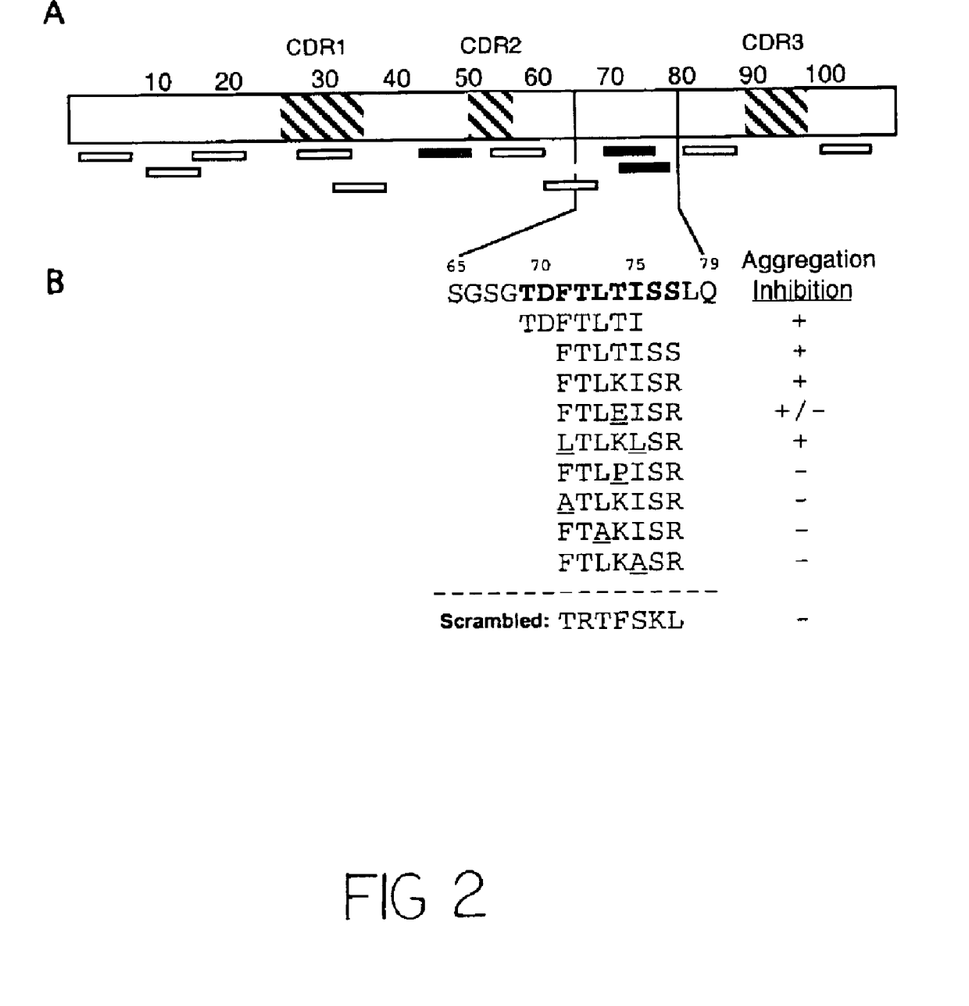
FIG. 2A depicts a region of a variable light chain from which anti-fibril-forming peptides are derived, in accordance with features of the present invention.
FIG. 2B depicts heptameric residues and their ability to stymie fibril formation, in accordance with features of the present invention.
Figures 3, 3A:
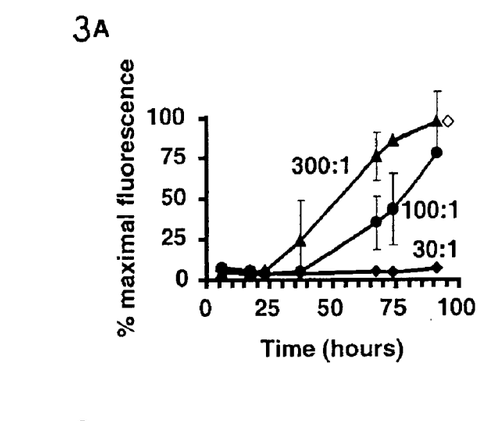
FIGS. 3A–3F graphically depicts data showing inhibition of fibrillogenesis by binding protein in accordance with features of the present invention.
Figures 3, 3B:
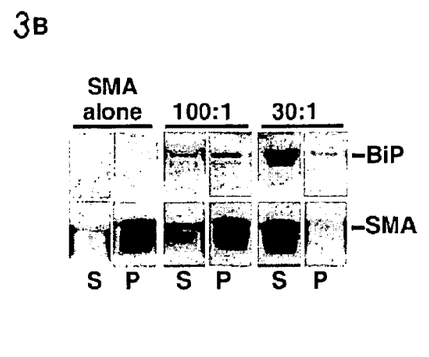
Figures 3, 3C:
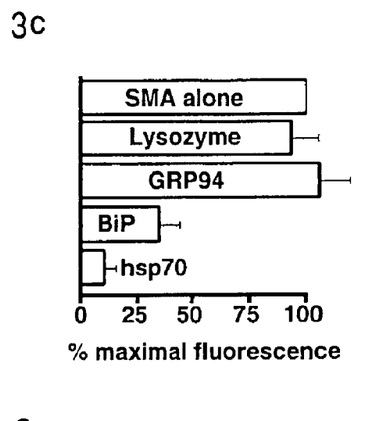
Figures 3, 3D:
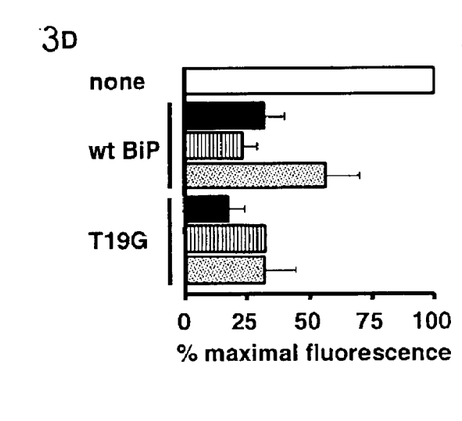
Figures 3, 3E:
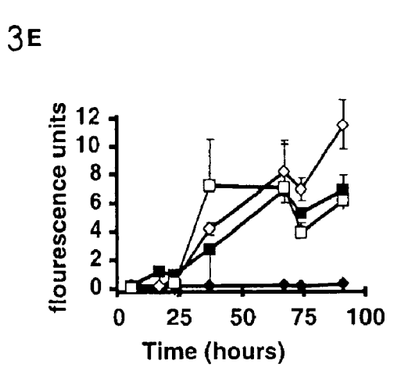
Figures 3, 3F:
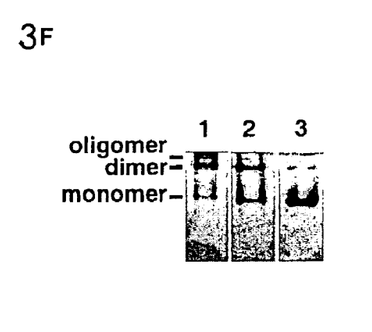

The inventors found that certain peptides stymie fibril formation otherwise seen in some mutated light chains. As noted in FIGS. 2A–2C, certain heptameric peptides derived from the $V_L$ sequence inhibit SMA fibrillogenesis. Each of the peptides emulates a straight span of one beta strand between two turns on the domain involved in fibril formation. The effectiveness of each peptide is indicated in FIG. 2B. Regions of the sequence which provide fibril inhibitors are indicated by black bars, with a prominent region being from residue position 69 to 79. Regions of the sequence not providing effective fibril blocking peptides are indicated in white bars, and include the region spanning residue number 1 through 7.

FIG. 2C compares the dose dependent inhibition of a fibril blocking peptide FTLTISS (SEQ. ID. NO. 1) and an ineffective fibril blocker TRIFSKL (SEQ. ID. NO. 2). Fibril formation was measured over time at each peptide concentration. The extent of SMA fibril formation at 45 hours in the presence of various concentration so fthe peptides is plotted relative to that of SMA alone at 45 hours. This time point was chosen because it was the time required for half-maximal fibril formation with no inhibitor present.

Binding Protein
Inhibition Detail

In the cellular environment, the endoplasmic reticulum (ER) chaperone BiP is important for regulating the folding of the $V_L$ domain and putative BiP binding sites on the $V_L$ were recently mapped. BiP, which stands for binding protein, can itself be bound to a target protein to stymie fibril formation. Chaperones are proteins that mediate correct assembly by causing a target protein to acquire one possible conformation instead of others. Chaperones influence the folding process by directing it toward productive assembly of the correct conformation rather than unproductive alternatives. This process is involved in initial acquisition of the correct conformation. Stable interactions form between parts of the protein that do not interact in the correct conformation when a protein is denatured. When a protein transiently mis-folds as it is initially synthesized, the protein is recognized by chaperones in the same way as comprising incorrect folds. This process is involved in recognizing a protein that has been denatured, and either assisting renaturation or leading to its removal by degradation.

As illustrated in FIG. 3, inclusion of BiP in the in vitro seeded SMA aggregation reaction dramatically inhibited fibril assembly and increased the $V_L$ fraction that remained soluble. BiP's effect was specific, since proteins like lysozome, albumin and ferritin did not significantly decrease fibril formation (See FIG. 3C). BiP captures the mobile loop bearing the alternate hydrophobic side-chains, inhibiting the ability to add aggregating units to the polymer, as well as possibly 'capping' the nuclei of polymerization. The free 69–77 peptide can act as a competitive inhibitor by occupying a crevice vacated by that segment during partial domain unfolding.

In the BiP reactions, SMA fibril formation was assayed in the range of 1 to 1000 moles SMA per mole of fibril antagonist.

FIG. 3A depicts a dose-dependent inhibition of SMA fibril formation by recombinant BiP. For example, at 30 SMA:1 BiP (diamonds), inhibition was very evident at less than 10 percent of the original fluorescence units. At a 100:1 stoichiometric ratio (circles), inhibition was still noted with 75 percent lower fluorescence recorded at early time points. At a 300:1 stoichiometric ratio, 100 percent fluorescence was recorded (triangles) without inhibition.

Another ER chaperone, GRP94, did not inhibit fibril formation as noted in FIG. 3C, with 100 percent maximal fluorescence observed. However, heat shock protein (hsp) 70, a family member of BiP, did inhibit fibril formation. Additionally, BiP prevented the ordered aggregation at vastly sub-stoichiometric ratios: as little as 1 mole per 100 moles of SMA exhibited 50% inhibition at 75 hours after mixing. The major effect of BiP was to increase the lag time of aggregation, rather than to reduce the final extent of aggregation. Addition of BiP to preformed fibrils did not reverse the aggregation. These data suggest that BiP is an inhibitor of the formation of a nucleation intermediate, presumably the rate-limiting part of the aggregation reaction, much like in Aβ or prion aggregation.

The ability of BiP to inhibit SMA fibril assembly was dependent on its peptide binding capacity. Cycles of binding and release are not essential for BiP inhibition of fibril formation. As can be noted in FIG. 3D, wild type BiP without added nucleotide (black bars) or in the presence of ADP (striped bars) inhibited fibril formation equivalently, while addition of ATP (stippled bars) decreased the efficiency of BiP inhibiting fibrillogenesis. Further, a BiP mutant with a substitution in the nucleotide binding site (T19G) inhibited fibril assembly as effectively as wild type BiP. This mutant is locked in the high affinity binding state, since upon nucleotide binding T19G BiP cannot transmit a conformational change in the peptide binding domain and release the substrate.

As depicted in FIG. 3E, prebinding BiP with the peptide FYQLALT (SEQ. ID. NO. 3), which is a high affinity pan-hsp70 substrate not derived from light chain, blocked the chaperone's ability to suppress fibril assembly. The filled diamonds in the graph depict good fibril depression if BiP is not incubated in the presence of the peptide prior to aggregation reaction. Conversely, when BiP is incubated in the presence of the peptide prior to addition to standard aggregation reaction, fibril prevention ability decreases. As in FIG. 3C, Lysozyme showed no appreciable fibril blocking ability, either alone (filled squares) or when pretreated with the peptide (open squares).

Furthermore, BiP progressively converts to its monomeric form upon incubation with SMA, as observed for BiP-peptide interactions. BiP binds to the aggregating $V_L$ unit and/or prevents formation of the nucleation intermediate. Since BiP is present in the ER of plasma cells at a vast molar excess compared to light chain, its activity may explain why light chain amyloids are commonly found as extracellular aggregates rather than intra cellularly.

Peptides derived from the $V_L$ sequence, including known BiP-binding peptides, were tested for their ability to prevent SMA fibril formation. Eighteen synthetic peptides spanning most of the $V_L$ sequence were tested. Among the eighteen synthetic peptides were FTLEISR (SEQ ID NO: 12) and LTLKLSR (SEQ ID NO: 13). Of them, PKLLIYWA, (SEQ ID NO. 4) (44–51) exhibited partial inhibition and the overlapping peptides TDFTLTI (SEQ ID NO. 5) (amino acids 69–75) and FTLTISS (SEQ ID NO. 1) (71–77) markedly inhibited the aggregation. The peptide FTLKISR, (SEQ ID NO. 6) a 71–77 sequence common to a number of $V_L$ germline genes inhibited as well as FTLTISS (SEQ ID NO. 1) and also inhibited fibril assembly of the peptide λ6 $V_L$ protein. Specific structural features of the sequence 71–77 are important for inhibiting aggregation. Peptides in which Phe71 or Ile75 were replaced by Leu were effective inhibitors. However, a peptide with the same amino acids as in the native sequence but, in a scrambled order did not inhibit, nor did any of the peptides with Phe71, Leu73 or Ile75 in FTLKISR (SEQ ID NO. 6) replaced by Ala. Placement of a Pro in a middle of the peptide also abolished its inhibitory capacity, suggesting that the extended conformation of the peptide is essential.

The inventors have found that the same features of the peptide required for inhibiting aggregation are also necessary for this peptide's binding to BiP. The ability of both BiP and its target $V_L$ peptide to inhibit aggregation therefore suggests that under aggregation-promoting conditions, the loop containing the TDFTLTISS (SEQ ID NO. 7) peptide in SMA is not anchored properly in the body of the V domain. The peptide inhibits fibril formation through interactions between its hydrophobic patch on partially unfolded SMA that mimics the BiP binding site.

The readiness with which SMA adopts fibrillogenic conformation as compared to LEN must be due to the minimal sequence differences between the two.

In addition to suggesting a molecular mechanism for light chain amyloidosis, the inventors' results also imply that many somatic mutants of immunoglobulin are involved in such aggregation. Only one (or a few) destabilizing mutation (s) is required to convert a soluble protein to an aggregate prone variation. Further, even if such a mutant does not aggregate spontaneously, it may be induced to form fibrils by the presence of another aggregating light chain, a potentially common in vivo event. Identification of these specific structural features should facilitate future development of rational strategies for drug discovery across the spectrum of amyloid disease.

In Vivo Aggregation Inhibition Detail

The complete LC of SMA or LEN have been expressed in COS cells. The inventors found that amyloidogenic protein can aggregate intracellularly. Unlike LEN, SMA is slow to fold and is readily recognized as an unstable protein; it is dislocated into the cytosol, where it either aggregates into inclusion bodies or is degraded by proteasomes. The chaperone Hsp70 interacts with SMA in the cytosol and plays an important role in its fate. Over-expression of Hsp70 improves the solubility of SMA and decreases its aggregation.

The inventors found that the same molecular surface required for fibril formation in vitro is important for aggregation in vivo. The same Hsp70-binding peptide which we showed to inhibit fibril assembly in vitro prevents aggregation of SMA in cells. This ability to modulate the degree of intracellular LC aggregation with chaperones and peptides suggests that rationally designed peptides may provide effective treatment modalities for a variety of amyloidoses.

Plasmids: For the purpose of expressing SMA and LEN in vivo, expression plasmids were constructed that direct the synthesis of complete kappa chains, containing either of these two variable region sequences followed by the constant region of human $C_x$, as disclosed by Hieter et al., Cell, 22, 197–207, and incorporated herein by reference. Pulse-chase analysis of COS cells transiently expressing these chains revealed that LEN was secreted as a wild type LC, but that SMA was not secreted.

Constructs directing expression of the complete SMA and LEN LC, wild type BiP and T19G BiP are disclosed in the Davis paper, earlier incorporated by reference herein. An Hsp70 expression plasmid was constructed by PCR amplification of the inducible gene from the pETWThsp70 vector (Abravaya et al., 1992). Amplified material was inserted into the vector pcDNA3.1 (Invitrogen, Carlsbad, Calif.).

COS-1 cells were transiently transfected with FuGENE 6 transfection reagent (Roche Molecular Biochemicals, Indianapolis, Ind.) according to manufacturer's instructions and analyzed two days later. Overnight incubations with various concentrations of ALLN (SEQ. ID. NO. 11) (Sigma Chemical Co., St. Louis, Mo.), 10 µM lactacystin (Calbiochem, La Jolla, Calif.), 10 µg/ml nocodazole (Sigma), or various concentrations of peptides were begun the day following transfection.

Culture, metabolic labeling, lysis and immunoprecipitation of COS-1 cells were performed as described in Dul et al. Immunol. 149, 1927–1933 (1992), and incorporated herein by reference. The following antibodies were used in immunoprecipitations: rabbit anti-human kappa antibody (Bethyl Labs, Montgomery, Tex.); goat anti-human kappa (Caltag, Burlingame, Calif.); mouse anti-ubiquitin (StressGen, Victoria, BC, Canada).

Cells were transfected in 6-well dishes and lysed in the wells with 200 µl each of the following buffer: 50 mM Tris-HCl, pH 8.0, 150 mM NaCl, 5 mM KCl, 5 mM $MgCl_2$, 0.5% Triton X-100, 0.5% deoxycholate, and 20 mM NEM, supplemented with protease inhibitors (1 µg/ml each of leupeptin and pepstatin A; 10 µg/ml each of TLCK, TPCK and soybean trypsin inhibitor). The lysates were passed through a 25 gauge needle 10 times on ice. Insoluble material was recovered by centrifugation at 16,000 g for 15 min. Pellets were solubilized in 50 µl 60 mM Tris-HCl, pH 6.8, 5% SDS, 10% glycerol with 1 min of sonication in a cuphold sonicator, followed by 10 min of boiling. Samples were separated on 11% SDS-PAGE gels and transferred to nitrocellulose. Membranes were incubated with goat anti-human kappa(BioSource, Camarillo, Calif.)and HRP-conjugated donkey anti-goat IgG (Santa Cruz Biotechnology, Santa Cruz, Calif.); rabbit anti-VSV G (J. Burkhardt, Univ. of Chicago) and HRP-conjugated goat anti-rabbit IgG (Jackson ImmunoResearch, West Grove, Pa.); mouse anti-raf (Transduction Labs, Lexington, Ky.) and HRP-conjugated goat anti-mouse IgG (Jackson). Bound antibodies were detected with SuperSignal West Pico Chemiluminescent Substrate (Pierce, Rockford, Ill.). Blots were quantitated using scanning densitomitry and NIH image 1.6 software.

A peptide was synthesized that fused an HIV TAT sequence (YGRKKRRQRRR) (SEQ. ID. NO. 8) with the $V_L$ derived sequence which the inventors have shown inhibit fiber formation in vitro, discussed supra. To ensure adequate flexibility and solubility, additional $V_L$ sequence was added on both sides of the active 7-mer, generating the following sequence for the TAT-TISS peptide: $NH_2$-YGRKKRRQRRRSGSGTDFTLTISSLQAED-OH. (SEQ. ID. NO. 9) A control peptide was synthesized (TAT-PASS) in which the critical hydrophobic residues were substituted with alanines and the extended structure of the peptide destroyed by the addition of a proline ($NH_2$-YGRKKRRQRRRSGSGTDATAPASSLQAED-OH). (SEQ. ID. NO. 10) cells were treated with either peptide 24 h after transfection and incubated overnight in the presence of the indicated concentrations of ALLN. (SEQ. ID. NO. 4) Cells were then harvested for western blotting or immunofluorescence as described above.

As noted supra, recombinant Hsp70 blocked fibril formation by recombinant variable domains in vitro. BiP, the ER homologue of Hsp70, also prevented in vitro fibril formation, but was less efficient than Hsp70.

The inventors have found that BiP suppressed aggregation in vivo. In particular, a mutant BiP that is unable to release substrate (T19G BiP), caused a larger pool of SMA to be retained within the ER and decreased the frequency of aggresome formation. The inventors also found that co-expression of Hsp70 with SMA decreases the frequency of aggresome formation. Without ALLN (SEQ. ID. NO. 11) treatment 30% of the COS cells contained aggresomes as assayed by immunofluorescence. Addition of ALLN (SEQ. ID. NO. 11) increased the proportion to 75%, but co-expression of Hsp70 dramatically decreased the frequency of aggresomes to 12% whether or not ALLN (SEQ. ID. NO. 11) was present.

To further investigate the effects of Hsp70 and BiP on the aggregation of SMA in vivo, the inventors used a biochemical assay. The inventors found that forced interaction with these chaperones improves the fate of SMA. When BiP or T19G BiP were co-expressed with SMA, a modest effect on the pool size of soluble LC was observed, as compared to cells transfected with SMA alone. This effect was variable in the absence of ALLN (SEQ. ID. NO. 11), but consistently observed in the presence of ALLN. (SEQ. ID. NO. 11) Co-expression of either of these chaperones had no effect on the size of the insoluble SMA pool.

The inventors further found that over-expression of cytosolic Hsp70, had a dramatic effect on SMA aggregation, both quantitatively and qualitatively. The yield of insoluble SMA was reduced 3- to 8-fold, while that of soluble SMA was proportionately increased. Longer exposure of the same blot showed a decrease in the pool of ubiquitinated SMA only when Hsp70 is co-expressed. To demonstrate direct interaction between Hsp70 and SMA, soluble fractions from metabolically labeled cells were immunoprecipitated with anti-kappa antibody and analyzed with reducing SDS-PAGE. In cells co-transfected with Hsp70 and SMA, Hsp70 was specifically co-immunoprecipitated with SMA. Overexpression of an irrelevant cytosolic protein, serum glucocorticoid inducible kinase, did not result in association with SMA. Endogenous Hsp70 was also associated with SMA, but was not dramatically enriched. This indicates that overexpression of Hsp70 decreased the cytosolic aggregation and aggresome formation and improved the targeting of SMA for degradation by the proteasome.

Taken together, these experiments show that the fate of misfolded, amyloidogenic LC was altered by increased interactions with Hsp70 family chaperones on either side of the ER membrane: more SMA was retained in the ER, less was aggregated and more of it remained in a soluble state, whether in the lumen of the ER or in the cytosol. Since the majority of SMA at steady state is in the dislocated, cytosolic pool, BiP would be expected to have less of an effect than Hsp70 when the total cellular protein is analyzed and this is indeed what we observed.

The inventors also found that An Hsp70-binding peptide derived from the LC sequence inhibits SMA aggregation in vivo. To optimize delivery of the peptide to all cellular compartments, it was synthesized with the 11-mer sequence from the HIV TAT protein at the N-terminus (Gius et al., 1999). This TAT peptide (SEQ. ID. NO. 8) permits the transduction of denatured proteins across cell membranes rapidly and efficiently in an energy- and receptor-independent fashion. In addition to the test peptide, TAT-TISS (SEQ. ID. NO. 9), another TAT-fusion was employed as a specificity control. This peptide, TAT-PASS (SEQ. ID. NO. 10), contains four amino acid substitutions and does not inhibit fibril formation in vitro. SMA transfected cells were incubated overnight in the presence of increasing concentrations of ALLN (SEQ. ID. NO. 11) and 50 μM of each peptide. In the range of 1–10 μg/ml ALLN, (SEQ. ID. NO. 11) there was a progressive increase in the amount of SMA found in the soluble fraction on a per cell basis. Inclusion of the TAT-TISS (SEQ. ID. NO. 9) peptide dramatically reduced the amount of SMA recovered at all ALLN (SEQ. ID. NO. 11) concentrations tested. In contrast, the TAT-PASS (SEQ. ID. NO. 9) peptide had no effect. Incubation of the same blots with arti-raf antibody demonstrated that equal cell equivalents were loaded across the gel.

The inventors also determined the effect of different concentrations of peptide on SMA following treatment with 10 μg/ml ALLN. (SEQ. ID. NO. 11) The TAT-TISS (SEQ. ID. NO. 9) peptide decreased the yield of SMA In the insoluble fractions much more than in the detergent soluble fractions. The magnitude of the decrease was from 4 to 10-fold (n=3), in a peptide concentration-dependent fashion, whereas the TAT-PASS (SEQ. ID. NO. 10) peptide had only a marginal effect even at the highest concentration used. As observed with co-expression of Hsp70, upon addition of the TAT-TISS (SEQ. ID. NO. 9) peptide, the ubiquitinated forms of SMA were diminished. This indicated that they were being maintained in a soluble form long enough to be kept off the aggregation pathway and were degraded by the proteasome.

Lastly, the inventors determined that the decrease in steady state level of SMA in the presence of TAT-TISS (SEQ. ID. NO. 9) peptide correlated with a decrease in the frequency of aggresome formation, by scoring anti-kappa stained cells. Roughly 30% of untreated cells exhibited aggresomes and this number increased to about 65% upon addition of ALLN. (SEQ. ID. NO. 11) Transduction of TAT-TISS (SEQ. ID. NO. 9) decreased the number of aggresomes by more than half, to 25%, about the same as in untreated cells, whereas addition of TAT-PASS (SEQ. ID. NO. 10) peptide had no significant effect. Hence, the large decrease in insoluble SMA observed in the presence of TAT-TISS (SEQ. ID. NO. 9) peptide coincides with a drop in aggresome formation.

In summary, the inventors have found that peptides which mimic the structure of amyloid-forming proteins are suitable agents in inhibiting fibril formation. Insertion of the peptides into a particular groove typically occupied by an adjacent fibril unit interrupts fibril assembly and thus prevents fibril formation.

When amyloidogenic light chain (LC) fails to fold properly it is dislocated out of the endoplasmic reticulum to the cytosol where two linked coping mechanism are present. While much of the expelled light chain is degraded by proteasomes, another fraction of the light chain aggregates. The inventors found that the introduction of a specific peptide into the cell inhibits aggregation and increases the efficiency of LC degradation.

The presence of a non-releasing BiP mutant (or high levels of wild type BiP) traps SMA molecules in the ER lumen that would otherwise be disloacted to the cytosol for aggregation.

Alternatively, once dislocated, interaction of SMA with cytosolic Hsp 70 improves the efficiency of aggregation. Over-expression of Hsp 70 decreased the insoluble and ubiquitin-tagged pools of SMA that accumulate in the presence of proteasome inhibitors. In the absence of proteasome inhibitors, however, the level of endogenous Hsp 70 was sufficient to support degradation of most SMA light chains. The inventors have identified a kinetic competition between degradation and aggregation: when there is sufficient Hsp 70 present to keep SMA soluble, more of it gets degraded, but if the level of Hsp 70 is inadequate, then more SMA aggregates. SMA is a type of proteasomal substrate whose degradation is improved by chaperon interactions.

Figure 4:
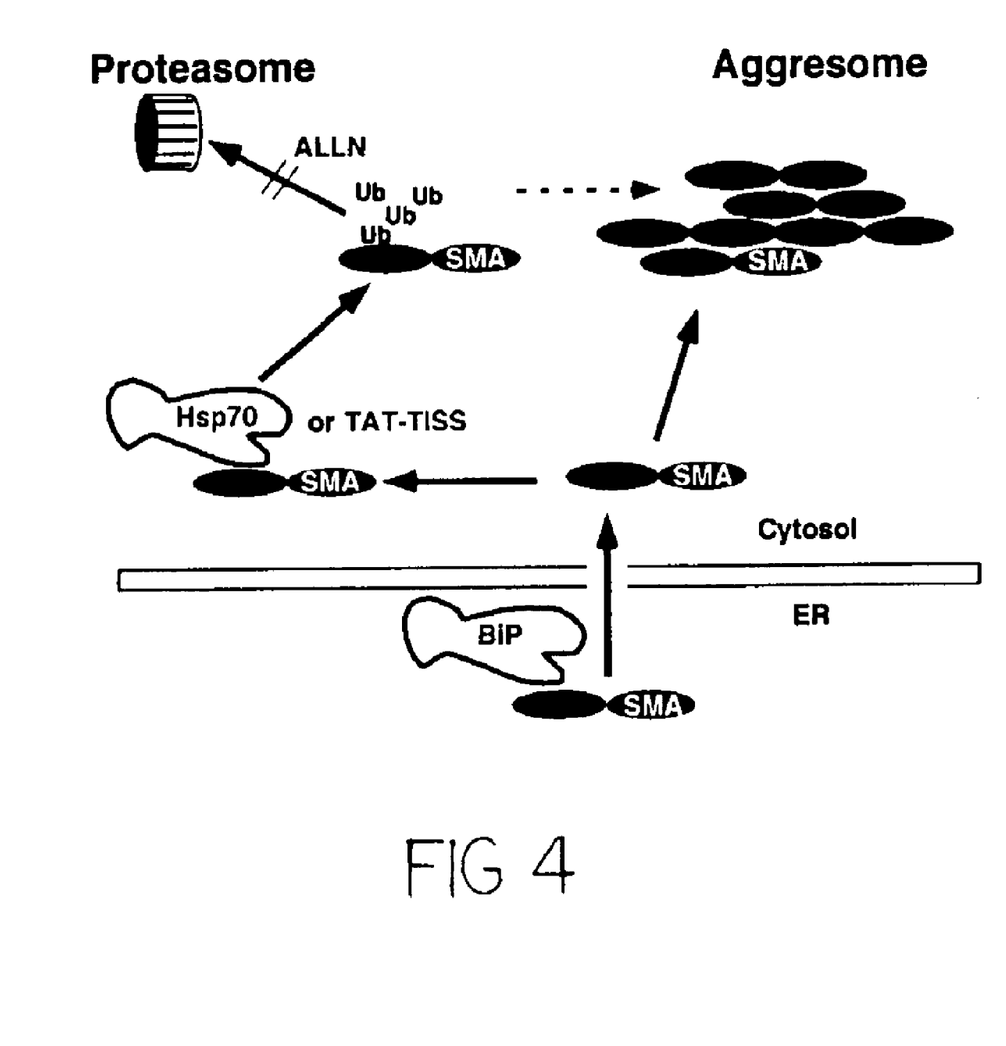
FIG. 4 depicts a schematic diagram of a method for aggregation inhibition in vivo, in accordance with features of the present invention

FIG. 4 depicts the inventor's competitive inhibition model. SMA fails to progress along a productive folding pathway and hence both of its domains remain in the reduced state in vivo. The presence of the highly unstable K4 protein is detected by BiP, presumably during or soon after its translocation across the ER membrane. Binding to BiP prevents SMA aggregation in the lumen and facilitates its dislocation back to the cytosol. Once there, binding to Hsp70 (or related chaperones) serves to maintain SMA in a degradation-competent state, so that it can be ubiquitinated and rapidly targeted to proteasomes. At the same time, Hsp70 inhibits the tendency of SMA to aggregate in the cytosol, thus regulating the balance between degradation and aggregation.

The inability to fold exposes (at least) the two major peptides in each of the two β sheets of the V domain that are good sites for binding of Hsp70 family chaperones. Continued exposure of these sites enables associations first with BiP (within the ER) and then with Hsp70 (in the cytosol). The FTLTISS (SEQ. ID. NO: 1) peptide which is effective in reducing intracellular aggregation has the sequence of one of these two major sites, and importantly, the same features that are required for its anti-aggregation activity are necessary for its Hsp70 binding activity.

The inventors envisage the peptide to interact with the same amino acids in the hydrophobic core of the V domain normally occupied in the folded molecule by the endogenous FTLTISS (SEQ. ID. NO: 1) peptide. In this way, the peptide acts as a surrogate chaperone, inhibiting aggregation and promoting degradation. This provides a new avenue for treatment modalities using rationally designed peptides to suppress aggregation.

While the invention has been described through the embodiments disclosed herein, it should be noted that the embodiments are not intended to limit the scope of the following claims.

The invention in which an exclusive right is asserted is claimed as follows:

1. A method for minimizing the aggregation tendencies of human kappa-IV immunoglobulin light chain, the method comprising: inserting a $V_L$ derived peptide into the complimentary region of the light chain variable domain of said human kappa-IV immunoglobulin light chain wherein said peptide consists the amino acid sequence selected from the group consisting of TDFTLTI (SEQ ID NO: 5), FTLTISS (SEQ ID NO: 1), FTLKISR (SEQ ID NO: 6), FTLEISR (SEQ ID NO: 12), LTLKLSR (SEQ ID NO: 13) and combinations thereof.

2. The method as recited in claim 1 wherein the peptide is inserted between residue position numbers 60 and 83 of the human kappa-IV light chain.

3. The method as recited in claim 1 wherein the pep-tide is inserted when the human kappa-IV immunoglobulin light chain is partially unfolded.

4. The method as recited in claim 2 wherein said position is a hairpin anchorage point in the human kappa-IV light chain.

5. A method for preventing fibril assembly of human kappa-IV immunoglobulin, the method comprising: inserting a $V_L$ derived peptide into the complimentary region of the light chain variable domain of said human kappa-IV immunoglobulin wherein said peptide consists the amino acid sequence selected from the group consisting of TDFTLTI (SEQ ID NO: 5), FTLTISS (SEQ ID NO: 1), FTLKISR (SEQ ID NO: 6), FTLEISR (SEQ ID NO: 12), LTLKLSR (SEQ ID NO: 13) and combinations thereof.

6. The method as recited in claim 5 wherein the peptide is derived from human kappa-IV immunoglobulin light chain.

7. The method as recited in claim 5 wherein the peptide is inserted when the human kappa-IV immunoglobulin is partially unfolded.

* * * * *

UNITED STATES PATENT AND TRADEMARK OFFICE
CERTIFICATE OF CORRECTION

PATENT NO. : 6,878,521 B1
DATED : April 12, 2005
INVENTOR(S) : Stevens et al.

It is certified that error appears in the above-identified patent and that said Letters Patent is hereby corrected as shown below:

Column 1,
Line 4, please insert the following paragraph:
-- CONTRACTUAL ORGIN OF THE INVENTION
The United States Government has rights in this invention pursuant to Contract Number W-31-109-ENG-38 between the U.S. Department of Energy and the University of Chicago representing Argonne National Laboratory --

Signed and Sealed this

Second Day of August, 2005

JON W. DUDAS
*Director of the United States Patent and Trademark Office*

UNITED STATES PATENT AND TRADEMARK OFFICE
CERTIFICATE OF CORRECTION

PATENT NO. : 6,878,521 B1
APPLICATION NO. : 09/712819
DATED : April 12, 2005
INVENTOR(S) : Fred J. Stevens et al.

Page 1 of 1

It is certified that error appears in the above-identified patent and that said Letters Patent is hereby corrected as shown below:

Column 1
Line 4, please amend the CONTRACTUAL ORIGIN paragraph to read as follows:

"The United States Government has rights in this invention pursuant to Contract Number W-31-109-ENG-38 between the U.S. Department of Energy and the University of Chicago representing Argonne National Laboratory, and also pursuant to Contract Number AI030178 awarded by the U.S. National Institutes of Health."

Signed and Sealed this

Eighteenth Day of November, 2008

JON W. DUDAS
*Director of the United States Patent and Trademark Office*

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
        (A) LENGTH: 7 amino acids
        (B) TYPE: amino acid
        (C) STRANDEDNESS: Single
        (D) TOPOLOGY: linear (xi) SEQUENCE DESCRIPTION: SEQ ID NO: 1:

Phe Thr Leu Thr Ile Ser Ser
1               5

(2) INFORMATION FOR SEQ ID NO: 2:

(i) SEQUENCE CHARACTERISTICS:
        (A) LENGTH: 7 amino acids
        (B) TYPE: amino acid
        (C) STRANDEDNESS: Single
        (D) TOPOLOGY: linear (xi) SEQUENCE DESCRIPTION: SEQ ID NO: 2:

Thr Arg Ile Phe Ser Lys Leu
1               5

(2) INFORMATION FOR SEQ ID NO: 3:

(i) SEQUENCE CHARACTERISTICS:
        (A) LENGTH: 7 amino acids
        (B) TYPE: amino acid
        (C) STRANDEDNESS: Single
        (D) TOPOLOGY: linear (xi) SEQUENCE DESCRIPTION: SEQ ID NO: 3:

Phe Tyr Gln Leu Ala Leu Thr
1               5

(2) INFORMATION FOR SEQ ID NO: 4:

(i) SEQUENCE CHARACTERISTICS:
        (A) LENGTH: 8 amino acids
        (B) TYPE: amino acid
        (C) STRANDEDNESS: Single
        (D) TOPOLOGY: linear (xi) SEQUENCE DESCRIPTION: SEQ ID NO: 4:

Pro Lys Leu Leu Ile Tyr Trp Ala
1               5

(2) INFORMATION FOR SEQ ID NO: 5:
        (A) LENGTH: 7 amino acids
        (B) TYPE: amino acid
        (C) STRANDEDNESS: Single
        (D) TOPOLOGY: linear (xi) SEQUENCE DESCRIPTION: SEQ ID NO: 5:

Thr Asp Phe Thr Leu Thr Ile
1               5

(2) INFORMATION FOR SEQ ID NO: 6:

(i) SEQUENCE CHARACTERISTICS:

```
        (A) LENGTH: 7 amino acids
        (B) TYPE: amino acid
        (C) STRANDEDNESS: Single
        (D) TOPOLOGY: linear (xi) SEQUENCE DESCRIPTION: SEQ ID NO: 6:

Phe Thr Leu Lys Ile Ser Arg
1               5

(2) INFORMATION FOR SEQ ID NO: 7:

(i) SEQUENCE CHARACTERISTICS:
        (A) LENGTH: 9 amino acids
        (B) TYPE: amino acid
        (C) STRANDEDNESS: Single
        (D) TOPOLOGY: linear (xi) SEQUENCE DESCRIPTION: SEQ ID NO: 7:

Thr Asp Phe Thr Leu Thr Ile Ser Ser
1               5

(2) INFORMATION FOR SEQ ID NO: 8

(i) SEQUENCE CHARACTERISTICS:
        (A) LENGTH: 11 amino acids
        (B) TYPE: amino acid
        (C) STRANDEDNESS: Single
        (D) TOPOLOGY: linear (xi) SEQUENCE DESCRIPTION: SEQ ID NO: 8:

Tyr Gly Arg Lys Lys Arg Arg Gln Lys Lys Lys
1               5                   10

(2) INFORMATION FOR SEQ ID NO: 9

(i) SEQUENCE CHARACTERISTICS:
        (A) LENGTH: 29 amino acids
        (B) TYPE: amino acid
        (C) STRANDEDNESS: Single
        (D) TOPOLOGY: linear (xi) SEQUENCE DESCRIPTION: SEQ ID NO: 9:

Tyr Glu Arg Lys Lys Arg Arg Gln Arg Arg Arg Ser Gly Ser Gly
1               5                   10                  15

Thr Asp Phe Thr Leu Thr Ile Ser Ser Leu Gln Ala Glu Asp
                20                  25

(2) INFORMATION FOR SEQ ID NO: 10

(i) SEQUENCE CHARACTERISTICS:
        (A) LENGTH: 29 amino acids
        (B) TYPE: amino acid
        (C) STRANDEDNESS: Single
        (D) TOPOLOGY: linear (xi) SEQUENCE DESCRIPTION: SEQ ID NO: 10:

Tyr Glu Arg Lys Lys Arg Arg Gln Arg Arg Arg Ser Gly Ser Gly
1               5                   10                  15

Thr Asp Ala Thr Ala Pro Ala Ser Ser Leu Gln Ala Glu Asp
                20                  25

(2) INFORMATION FOR SEQ ID NO: 11:

(i) SEQUENCE CHARACTERISTICS:
        (A) LENGTH: 4 amino acids
        (B) TYPE: amino acid
        (C) STRANDEDNESS: Single
```

-continued

```
        (D) TOPOLOGY: linear (xi) SEQUENCE DESCRIPTION: SEQ ID NO: 11:

Ala Leu Leu Asn
1

(2) INFORMATION FOR SEQ ID NO: 12:

(i) SEQUENCE CHARACTERISTICS:
        (A) LENGTH: 7 amino acids
        (B) TYPE: amino acid
        (C) STRANDEDNESS: Single
        (D) TOPOLOGY: linear (xi) SEQUENCE DESCRIPTION: SEQ ID NO: 12:

Phe Thr Leu Glu Ile Ser Arg
1               5

(2) INFORMATION FOR SEQ ID NO: 13:

(i) SEQUENCE CHARACTERISTICS:
        (A) LENGTH: 7 amino acids
        (B) TYPE: amino acid
        (C) STRANDEDNESS: Single
        (D) TOPOLOGY: linear (xi) SEQUENCE DESCRIPTION: SEQ ID NO: 13:

Leu Thr Leu Lys Leu Ser Arg
1               5
```